(12) United States Patent
Fuchss

(10) Patent No.: US 7,329,677 B2
(45) Date of Patent: Feb. 12, 2008

(54) IMIDAZO(4,5-B)PYRIDINE-DERIVATIVES AS INDUCIBLE NO-SYNTHASE INHIBITORS

(75) Inventor: Thomas Fuchss, Radolfzell (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/573,203

(22) PCT Filed: Sep. 30, 2004

(86) PCT No.: PCT/EP2004/052370

§ 371 (c)(1),
(2), (4) Date: Mar. 24, 2006

(87) PCT Pub. No.: WO2005/030768

PCT Pub. Date: Apr. 7, 2005

(65) Prior Publication Data

US 2007/0010549 A1 Jan. 11, 2007

(30) Foreign Application Priority Data

Oct. 1, 2003 (EP) ................................. 03022042

(51) Int. Cl.
*A61K 31/44* (2006.01)
*C07D 498/02* (2006.01)
*C07D 513/02* (2006.01)
*C07D 515/02* (2006.01)
(52) U.S. Cl. ...................... 514/303; 546/118
(58) Field of Classification Search ................ 546/118; 514/303
See application file for complete search history.

(56) References Cited

U.S. PATENT DOCUMENTS

| 4,045,564 | A | 8/1977 | Berntsson et al. |
| 7,138,399 | B2 | 11/2006 | Ulrich |

FOREIGN PATENT DOCUMENTS

| DE | 25 04 252 C2 | 8/1975 |
| EP | 0 125 756 A2 | 11/1984 |
| WO | 97/25030 A1 | 7/1997 |
| WO | 00/49015 A1 | 8/2000 |
| WO | 03/080607 | * 10/2003 |
| WO | 03/080607 A1 | 10/2003 |
| WO | 2005/030769 A1 | 4/2005 |
| WO | 2005/030770 A1 | 4/2005 |
| WO | 2005/030771 A1 | 4/2005 |
| WO | 2005/061496 A1 | 7/2005 |

OTHER PUBLICATIONS

Kiss et al., European Journal of Pharmacology, "Time-dependent actions of nitric oxide synthase inhibition on colonic inflammation induced by trinitrobenzene sulphonic acid in rats", 1997, vol. 336, pp. 219-224.*

Agostino et al., European Journal of Pharmacology, "Tetracycline inhibits the nitric oxide synthase activity induced by endotoxin in cultured murine macrophages", 1998, vol. 346, p. 283-290.*

Hua, L.L., et al., "Role of mitogen-activated protein kinases in inducible nitric oxide synthase and TNFα expression in human fetal astrocytes", *Journal of Neuroimmunology*, vol. 126, pp. 180-189, (2002).

Kim, M-S, et al., "Water-soluble chitosan inhibits the production of pro-inflammatory cytokine in human astrocytoma cells activated by amyloid β peptide and interleukin-1β", *Neuroscience Letters*, vol. 321, pp. 105-109, (2002).

Sautebin, L., "Prostaglandins and nitric oxide as molecular targets for anti-inflammatory therapy", *Fitoterapia*, vol. 71, pp. S48-S57, (2000).

Ohtsuka, M., et al., "PPA250 [3-(2,4-Diflurophenyl)-6-{2-[4-(1H-imidazol-l-ylmethyl)Phenoxy]ethoxy}-2-phenylpyridine], a Novel Orally Effective Inhibitor of the Dimerization of Inducible Nitric-Oxide Synthase, Exhibits an Anti-Inflammatory Effect in Animal Models of Chronic Arthritis", *The Journal of Pharmacology and Experimental Therapeutics*, vol. 303, No. 1, pp. 52-57, (2002).

Hansel, T. T., et al., "A selective inhibitor of inducible nitric oxide synthase inhibits exhaled breath nitric oxide in healthy volunteers and asthmatics", *FASEB J*, vol. 17, pp. 1298-1300, (2003).

Tinker, A. C., et al., "1,2-Dihydro-4-quinazolinamines: Potent, Highly Selective Inhibitors of Inducible Nitric Oxide Synthase Which Show Antiinflammatory Activity in Vivo", *J. Med. Chem.*, vol. 46, pp. 913-916, (2003).

Kankuri, E., et al., "Suppression of Acute Experimental Colitis by a Highly Selective Inducible Nitric-Oxide Synthase Inhibitor, N-[3-(Aminomethyl)benzyl]acetamidine", *The Journal of Pharmacology and Experimental Therapeutics*, vol. 298, No. 3, pp. 1128-1132, (2001).

Liu, Z-Q, et al., "Specificity of inducible nitric-oxide synthase inhibitors: prospects for their clinical therapy", *Acta Pharmacol Sin*, vol. 20, No. 11, pp. 1052-1056, (1999).

Salvemini, D., et al., "Dual Inhibition of Nitric Oxide and Prostaglandin Production Contributes to the Antiinflammatory Properties of Nitric Oxide Synthase Inhibitors", *J. Clin. Invest.*, vol. 96, pp. 301-308, (1995).

Cuzzocrea, S., et al., "Beneficial effects of GW274150, a novel, potent and selective inhibitor of INOA activity, in a rodent model of collagen-induced arthritis", *European Journal of Pharmacology*, vol. 453, pp. 119-129, (2002).

* cited by examiner

*Primary Examiner*—Margaret D. Seaman
*Assistant Examiner*—Niloofar Rahmani
(74) *Attorney, Agent, or Firm*—The Nath Law Group; Joshua B. Goldberg; Sheldon M. McGee

(57) ABSTRACT

The compounds of formula (I)

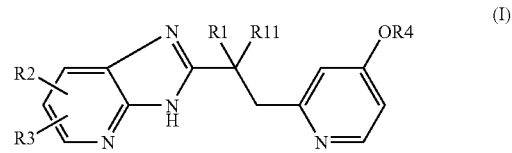

in which R1, R2, R3, R4 and R11 have the meanings as given in the description are novel effective iNOS inhibitors.

6 Claims, No Drawings

IMIDAZO(4,5-B)PYRIDINE-DERIVATIVES AS INDUCIBLE NO-SYNTHASE INHIBITORS

This application was filed under 35 U.S.C. 371 as a national stage of PCT/EP2004/052370, filed Sep. 30, 2004.

FIELD OF APPLICATION OF THE INVENTION

The invention relates to novel imidazo[4,5-b]pyridine derivatives, which are used in the pharmaceutical industry for the production of pharmaceutical compositions.

KNOWN TECHNICAL BACKGROUND

In the German Patent Application DE 2504252 and in the European Patent Application EP 0125756 3H-imidazo[4,5-b]pyridine derivatives with anti-ulcer activity are described.

The International Application WO 0049015 describes pyridine compounds with inhibitory activity on the production of nitric oxide.

DESCRIPTION OF THE INVENTION

It has now been found that the imidazo[4,5-b]pyridine derivatives, which are described in greater details below, have unanticipated and sophisticated structural features and surprising and particularly advantageous properties.

The invention thus relates to compounds of formula I

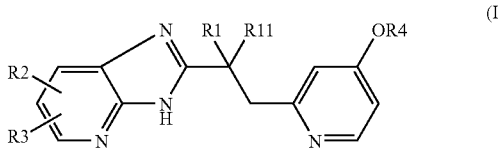

in which

R1 is hydrogen or 1-4C-alkyl,

R2 is hydrogen, halogen, hydroxyl, nitro, amino, 1-7C-alkyl, trifluoromethyl, 3-7C-cycloalkyl, 3-7C-cycloalkyl-1-4C-alkyl, 1-4C-alkoxy, completely or predominantly fluorine-substituted 1-4C-alkoxy, 1-4C-alkoxy-1-4C-alkyl, 1-4C-alkoxy-1-4C-alkoxy, 1-4C-alkoxycarbonyl, mono- or di-1-4C-alkylaminocarbonyl, mono- or di-1-4C-alkylaminosulfonyl, 1-4C-alkylcarbonylamino, 1-4C-alkylsulfonylamino, phenyl, R21- and/or R211-substituted phenyl, phenyl-1-4C-alkyl, phenyl-1-4C-alkyl wherein the phenyl moiety is substituted by R22, phenyl-1-4C-alkoxy, pyridyl, pyridyl substituted by R23, pyridyl-1-4C-alkyl, pyridyl-1-4C-alkyl wherein the pyridyl moiety is substituted by R24, in which R21 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, aminosulfonyl, mono- or di-1-4C-alkylaminosulfonyl, amino, mono- or di-1-4C-alkylamino, trifluoromethyl, hydroxyl, phenylsulfonylamino or phenyl-1-4C-alkoxy, R211 is halogen or 1-4C-alkoxy, R22 is halogen, 1-4C-alkyl or 1-4C-alkoxy, R23 is halogen, 1-4C-alkyl or 1-4C-alkoxy, R24 is halogen, 1-4C-alkyl or 1-4C-alkoxy, R3 is hydrogen, halogen, 1-4C-alkyl or 1-4C-alkoxy, R4 is 1-4C-alkyl, R11 is 1-4C-alkyl, and the salts, the N-oxides and the salts of the N-oxides of these compounds.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

1-4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, iso-propoxy, and, particularly, the ethoxy and methoxy radicals.

3-7C-Cycloalkyl stands for cyclopropyl, cyclobutyl, cyclopentyl, cyclohexyl and cycloheptyl, of which cyclopropyl, cyclobutyl and cyclopentyl are preferred.

3-7C-Cycloalkyl-1-4C-alkyl stands for one of the abovementioned 1-4C-alkyl radicals, which is substituted by one of the abovementioned 3-7C-cycloalkyl radicals. 3-7C-Cycloalkyl-1-2C-alkyl, particularly 3-7C-cycloalkylmethyl, radicals are to be emphasized in this connection. Examples which may be mentioned are the cyclopropylmethyl, the cyclohexylmethyl and the cyclohexylethyl radicals.

Halogen within the meaning of the present invention is iodine, bromine, chlorine or fluorine.

Completely or predominantly fluorine-substituted 1-4C-alkoxy is, for example, the 2,2,3,3,3-pentafluoropropoxy, the perfluorethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy groups are replaced by fluorine atoms.

1-4C-Alkoxy-1-4C-alkoxy stands for one of the abovementioned 1-4C-alkoxy radicals which is substituted by the same or another of the abovementioned 1-4C-alkoxy radicals. Examples which may be mentioned are the 2-(methoxy)ethoxy (-O-CH$_2$-CH$_2$-O-CH$_3$) and the 2-(ethoxy)ethoxy radical (-O-CH$_2$-CH$_2$-O-CH$_2$-CH$_3$).

1-4C-Alkoxy-1-4C-alkyl stands for one of the abovementioned 1-4C-alkyl radicals which is substituted by one of the abovementioned 1-4C-alkoxy radicals. Examples which may be mentioned are the 2-ethoxyethyl and the 3-methoxypropyl radical.

Mono- or Di-1-4C-alkylamino radicals contain in addition to the nitrogen atom, one or two of the abovementioned 1-4C-alkyl radicals. Preferred are the di-1-4C-alkylamino radicals, especially the dimethylamino, the diethylamino and the diisopropylamino radicals.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

Mono-or Di-1-4C-alkylaminosulfonyl stands for a sulfonyl group to which one of the abovementioned mono- or di-1-4C-alkylamino radicals is bonded. Examples which may be mentioned are the methylaminosulfonyl, the dimethylaminosulfonyl and the ethylaminosulfonyl radical.

An 1-4C-Alkylcarbonylamino radical is, for example, the propionylamino [C₃H₇C(O)NH-] and the acetylamino radical [CH₃C(O)NH-].

An 1-4C-Alkylsulfonylamino radical is, for example, the propylsulfonylamino [C₃H₇S(O)₂NH-] and the methylsulfonylamino radical [CH₃S(O)₂NH-].

1-4C-Alkoxycarbonyl is a carbonyl group to which one of the abovementioned 1-4C-alkoxy radicals is bonded. Examples are the methoxycarbonyl [CH₃O-C(O)-] and the ethoxycarbonyl [CH₃CH₂O-C(O)-] radicals.

Phenyl-1-4C-alkoxy stands for one of the abovementioned 1-4C-alkoxy radicals, which is substituted by the phenyl radical. Examples which may be mentioned are the benzyloxy and the phenethoxy radical.

Phenyl-1-4C-alkyl stands for one of the abovementioned 1-4C-alkyl radicals, which is substituted by a phenyl radical. Examples which may be mentioned are the phenethyl and the benzyl radical.

Pyridyl-1-4C-alkyl stands for one of the abovementioned 1-4C-alkyl radicals, which is substituted by a pyridyl radical. Examples which may be mentioned are the pyridylethyl and the pyridylmethyl radical.

N-oxide denotes the N-oxide on the pyridine which is substituted by OR4.

Compounds according to this invention which may be mentioned include for example compounds of formula Ia

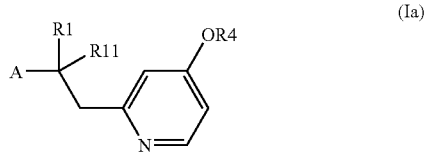

(Ia)

in which R1, R4 and R11 have the meanings given above and A suitably includes 3H-imidazo [4,5-b]pyridin-2-yl, 7-methyl-3H-imidazo[4,5-b]pyridin-2-yl, 5,7-dimethyl-3H-imidazo[4,5-b]pyridin-2-yl, 5-methoxy-3H-imidazo[4,5-b]pyridin-2-yl, 6-brom-3H-imidazo[4,5-b]pyridin-2-yl, 7-methoxy-3H-imidazo[4,5-b]pyridin-2-yl, 7-hydroxy-3H-imidazo[4,5-b]pyridin-2-yl, 7-ethoxy-3H-imidazo[4,5-b]pyridin-2-yl, 7-(2-methoxy-ethoxy)-imidazo[4,5-b]pyridin-2-yl, 7-(1,1,1-trifluoroethoxy)-3H-imidazo[4,5-b]pyridin-2-yl, 7-(phenylethoxy)-3H-imidazo[4,5-b]pyridin-2-yl, 7-(phenylethyl)-3H-imidazo[4,5-b]pyridin-2-yl, 7-(tolylethyl)-3H-imidazo[4,5-b]pyridin-2-yl, 7-(pyrid-4-ylethyl)-3H-imidazo [4,5-b]pyridin-2-yl, 7-(pyrid-2-ylethyl)-3H-imidazo[4,5-b]pyridin-2-yl, 7-(pyrid-3-ylethyl)-3H-imidazo[4,5-b]pyridin-2-yl, 7-(4-methoxypyrid-2-ylethyl)-3H-imidazo[4,5-b]pyridin-2-yl, 6-phenyl-3H-imidazo[4,5-b]pyridin-2-yl, 6-n-butyl-3H-imidazo[4,5-b]pyridin-2-yl, 6-(4-methoxyphenyl)-3H-imidazo[4,5-b]pyridin-2-yl, 6-(4-methylphenyl)-3H-imidazo[4,5-b]pyridin-2-yl, 6-nitro-3H-imidazo[4,5-b]pyridin-2-yl, 6-(pyrid-3-yl)-3H-imidazo[4,5-b]pyridin-2-yl, 6-(4-cyanophenyl)-3H-imidazo[4,5-b]pyridin-2-yl, 6-methyl-3H-imidazo[4,5-b]pyridin-2-yl, 6-trifluoromethyl-3H-imidazo[4,5-b]pyridin-2-yl, 6-iodo-3H-imidazo[4,5-b]pyridin-2-yl, 6-(4-aminophenyl)-3H-imidazo[4,5b]pyridin-2-yl, 6-(4-dimethylaminophenyl)-3H-imidazo[4,5b]pyridin-2-yl, 6-(4-hydroxyphenyl)-3H-imidazo[4,5b]pyridin-2-yl, 6-(4-trifluoromethylphenyl)-3H-imidazo[4,5-b]pyridin-2-yl, 6-(4-phenylsulfonylaminophenyl)-3H-imidazo[4,5-b]pyridin-2-yl, 6-(3,4dimethoxyphenyl)-3H-imidazo[4,5b]pyridin-2-yl, 6-(3,4-dichlorophenyl)-3H-imidazo[4,5-b]pyridin-2-yl, 6-(3,5-dichlorophenyl)-3H-imidazo[4,5-b]pyridin-2-yl, 6-(4-benzyloxyphenyl)-3H-imidazo[4,5-b]pyridin-2-yl, 6-(4-benzyloxy-3-fluoro-phenyl)-3H-im idazo[4,5-b]pyridin-2-yl, 6-(3-methyl-butyl)-3H-imidazo[4,5b]pyridin-2-yl, 6-cyclohexylmethyl-3H-imidazo[4,5b] pyridin-2-yl, 6-benzyl-3H-imidazo[4,5-b]pyridi n-2-yl, 6-ethyl-3H-imidazo[4,5-b]pyridin-2-yl, 6-isopropyl-3H-imidazo[4,5-b]pyridin-2-yl, 6-n-pentyl-3H-imidazo[4,5-b]pyridin-2-yl, 6-(4-chlorophenyl)-3H-imidazo[4,5-b]pyridin-2-yl, 6-(4-fluorophenyl)-3H-imidazo[4,5-b]pyridin-2-yl, 6-(24luorophenyl)-3H-imidazo[4,5-b]pyridin-2-yl, 6-(4-bromophenyl)-3H-imidazo[4,5-b]pyridin-2-yl, 6-(3-bromophenyl)-3H-imidazo[4,5-b]pyridin-2-yl, 6-(3-methylphenyl)-3H-imidazo[4,5-b]pyridin-2-yl, 6-phenethyl-3H-imidazo[4,5-b]pyridin-2-yl, 6(3phenylpropyl)-3H-imidazo [4,5-b]pyridin-2-yl, 6(4-bromo-phenyl-methyl)-3H-imidazo[4,5-b]pyridin-2-yl, 6-(4-acetamido-phenyl)-3H-imidazo[4,5-b]pyridin-2-yl, 6(4-methoxycarbonyl-phenyl)-H-imidazo[4,5-b]pyridin-2-yl, 6-(4-carboxy-phenyl)-3H-imidazo [4,5-b]pyridin-2-yl, 6-methoxycarbonyl-3H-imidazo[4,5-b]pyridin-2-yl, 6-(4-dimethylamino-carbonyl-phenyl)3H-imidazo[4,5b]pyridin-2-yl, 6-(4-dimethylaminosulphonyl-phenyl)-3H-imidazo [4,5-b] pyridin-2-yl, 6-(4-diethylaminosulphonyl-phenyl)-3H-imidazo[4,5-b]pyridin-2-yl, 6-(4-methylamino-sulphonyl-phenyl)-3H-imidazo[4,5-b]pyridin-2-yl, 6(4-aminosulphonyl-phenyl)-3H-imidazo [4,5-b]pyridin-2-yl, 6-(4-othylaminosulphonyl-phenyl)-3H-imidazo[4,5-b]pyridin-2-yl or 6-(3-luoro-4-dimethylaminosulphonyl-phenyl)-3H-imidazo [4,5b]pyridin-2-yl.

Suitable salts for compounds of formula I—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

A person skilled in the art knows on the base of his/her expert knowledge that the compounds according to this invention can exist, with regard to the fused imidazo ring, in different tautomeric forms such as e.g. in the 1-H form or, preferably, in the 3-H form, which is shown in formula I. The invention includes all conceivable tautomers in pure form as well as in any mixing ratio. Particularly the present invention includes the pure 1-H- and, preferably, 3-H-tautomers as well as any mixtures thereof.

Compounds according to this invention worthy to be mentioned are those compounds of formula I in which R1 is hydrogen or 1-4C-alkyl,
R2 is hydrogen,
R3 is hydrogen,
R4 is methyl,
R11 is 1-4C-alkyl, and the salts, the N-oxides and the salts of the N-oxides of these compounds.

Compounds according to this invention more worthy to be mentioned are those compounds of formula I in which either
R1 is hydrogen,
R2 is hydrogen,
R3 is hydrogen,
R4 is methyl, and
R11 is methyl or ethyl, or
R1 is methyl,
R2 is hydrogen,
R3 is hydrogen,
R4 is methyl, and
R11 is methyl, and the salts, the N-oxides and the salts of the N-oxides of these compounds.

The compounds of fornmula I according to the invention are, depending on the meanings of R1 and R11, chiral compounds. The invention includes all conceivable enantiomers in pure form as well as in any mixing ratio including the racemate.

A special embodiment of the compounds of the present invention include those compounds of formula I in which R4 is methyl.

Another special embodiment of the compounds of the present invention include those compounds of formula I in which R3 is hydrogen.

Another special embodiment of the compounds of the present invention include those compounds of formula I in which R4 is methyl and R3 is hydrogen.

Another special embodiment of the compounds of the present invention include those compounds of formula I in which R1 is hydrogen and R11 is methyl.

Another special embodiment of the compounds of the present invention include those compounds of formula I in which R1 is hydrogen, R4 is methyl and R11is methyl.

Another special embodiment of the compounds of the present invention include those compounds of formula I in which R1 is hydrogen, R3 is hydrogen, R4 is methyl and R11 is methyl.

Another special embodiment of the compounds of the present invention include those compounds of formula I in which the substituent R2 is bonded to the 6-position of the imidazopyridine ring system.

The substituents R2 and R3 of compounds of formula I according to this invention can be attached at any possible ring carbon atoms of the pyridine portion of the 3H-imidazo [4,5-b]pyridine ring system, whereby a special embodiment of the compounds of the present invention include those compounds of formula I in which R2 is bonded to the 6-position of the imidazopyridine ring system and R3 is hydrogen.

The substituents R21 and R211 can be attached in the ortho, meta or para position with respect to the binding position in which the phenyl ring is bonded to the imidazopyridine ring system, whereby in a special embodiment the substituent R21 is attached in the para position.

The compounds of formula I according to the invention can, for example, be prepared according to those synthesis routes specified and shown below or in a manner described by way of example in the following examples or analogously or similarly thereto.

Reaction scheme 1 below shows by way of example the preparation of compounds of formula I, in which R1 is hydrogen and R2, R3, R4 and R11 have the meanings indicated above.

Reaction scheme 1:

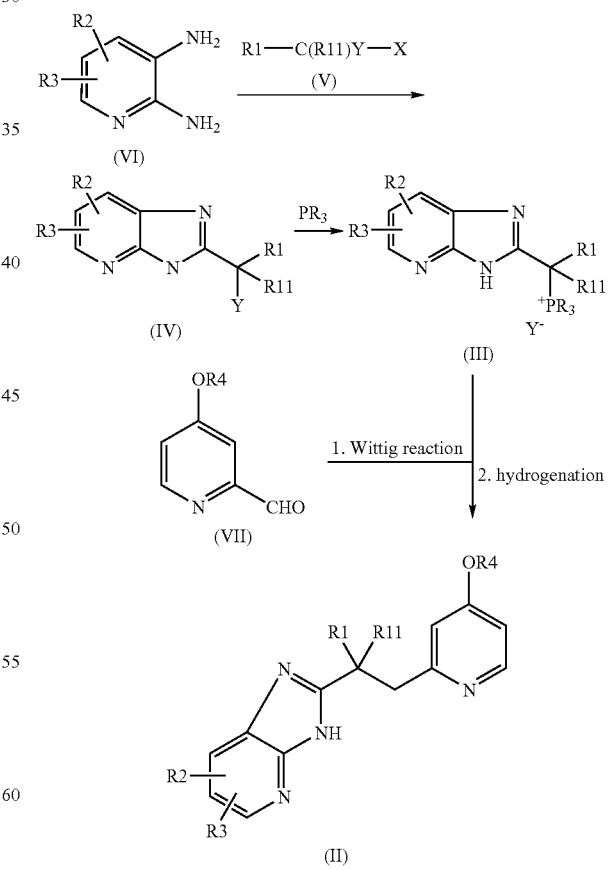

In a first reaction step diamino compounds of formula VI, in which R2 and R3 have the meanings indicated above, are converted into 3H-imidazo[4,5-b]pyridine derivatives in a manner known from the literature or with analogous or similar use of processes known from the literature. For example, said compounds of formula VI can be reacted with carboxylic acids or carboxylic acid derivatives of formula V, in which R1 is hydrogen, R11 has the meanings indicated above, Y is a suitable leaving group, advantageously chlorine, and X is a cyano or carboxyl radical, to give in a condensation reaction compounds of formula IV, in which R1 is hydrogen and R2, R3, R11 and Y have the meanings mentioned above. This condensation reaction can be carried out as known to one of ordinary skill in the art or as described by way of example in the following examples, for example, by using a suitable condensing agent such as preferably polyphosphoric acid in a suitable inert solvent or, preferably, without further solvent using an excess of condensing agent, preferably at elevated temperature, in particular at 130°-170° C.

Compounds of formula VI are commercially available or are known, e.g. from S.-X. Cai et al., J. Med. Chem. 1997, 40(22), 3679-3686, or can be obtained according to known procedures or analogously or similarly thereto.

Compounds of formula V are also commercially available or can be obtained in a known manner.

Alternatively, compounds of the formula IV, in which R1, R2, R3 and Y have the meanings mentioned above and R11 is hydrogen, can be also obtained by art-known procedures according to literature (e.g. as described in L. Bukowski et al., Pharmazie 1999, 54(9), 651-654 or G. Cleve et al. Liebigs Ann. Chem. 1971, 747, 158-171).

Compounds of formula IV, in which R1 is hydrogen and R2, R3, R11 and Y have the meanings mentioned above, can be converted with certain phosphanes into corresponding phosphonium salts. Preferably, compounds of formula IV are reacted with tributylphosphane or triphenylphosphane to give corresponding compounds of formula III, in which R1 is hydrogen and R2, R3, R11 and Y have the meanings mentioned above and R is butyl or phenyl. Said reaction can be carried out in a manner habitual per se or as described in the following examples in a suitable solvent such as, for example, acetonitrile or N,N-dimethylformamide or a mixture thereof, at elevated temperature, preferably at 90°-150° C., optionally in the presence of an auxiliary such as tetrabutylammonium iodide.

Compounds of formula III, in which R1 is hydrogen and R2, R3, R11 and Y have the meanings mentioned above and R is butyl or phenyl, are reacted with compounds of formula VII, in which R4 has the meanings given above. Said reaction can be carried out in a manner as described in the following examples or as known to the person skilled in the art according to a Wittig reaction. In the scope of this invention, said Wittig reaction is preferably carried out in a suitable solvent such as, for example, methanol or tetrahydrofurane, using a suitable base such as, for example, sodium hydride or sodium methanolate, at room temperature or at elevated temperature, preferably at 50°-80° C. With regard to the configuration of the exocyclic double bond obtained by Wittig reaction, the outcome can be a Z- or E-configurated product or, in particular, a mixture thereof.

The reduction of the abovementioned exocyclic double bond following the deprotection reaction leads to desired compounds of formula II, in which R1 is hydrogen and R2, R3, R4 and R11 have the meanings given above. This reaction can be carried out as hydrogenation reaction according to procedures known to the person skilled in the art or according to the following examples in the presence of a suitable catalyst, such as, for example, palladium on active carbon or platinum dioxide, in a suitable solvent (e.g. in a lower alcohol, such as, for example, methanol). If necessary, acid, such as trifluoracetic acid or acetic acid, can be added to the reaction mixture.

Compounds of formula VII, in which R4 has the meanings mentioned above, can be obtained, for example, as described in Ashimori et al. Chem. Pharm. Bull. 1990, 38, 2446-2458 or analogously or similarly thereto using process steps known to the person skilled in the art.

Reaction scheme 2 below shows by way of example the preparation of compounds of formula I, in which R1 is hydrogen or, preferably, 1-4C-alkyl and R2, R3, R4 and R11 have the meanings indicated above. In a first reaction step compounds of formula VII, in which R4 has the meanings mentioned above, are converted into ester compounds—preferably the methyl ester compounds—of formula IX, in which R1 is hydrogen or, preferably, 1-4C-alkyl and R4 and R11 have the meanings given above and R' is suitably methyl, in a manner known from the literature (e.g. according to an aldol reaction) or with analogous or similar use of processes known from the literature. For example, said compounds of formula VII can be reacted with suitable compounds of formula VIII, in which R1 is hydrogen or, preferably, 1-4C-alkyl and R11 has the meanings mentioned above and TMS represents trimethylsilyl, to obtain in an aldol reaction ester compounds—preferably the methyl ester compounds—of the formula IX, in which R1 is hydrogen or, preferably, 1-4C-alkyl and R4 and R11 have the meanings given above. This aldol reaction is carried out as described in the following examples or as known to one of ordinary skill in the art. With regard to the configuration of the carbon atom to which the hydroxyl group is bounded, the outcome of said aldol reaction can—depending on the reaction conditions—be a R- or S-configurated carbon atom or, in particular, a mixture thereof.

Said compounds of formula VIII are known and/or commercially available or they can be prepared according to art-known procedures or similarly or analogeously thereto.

In a second step the hydroxyl radical of ester compounds—preferably the methyl ester compounds—of formula IX, in which R1 is hydrogen or, preferably, 1-4C-alkyl and R4 and R11 have the meanings indicated above, is deoxygenated to give corresponding compounds of formula X. Said deoxygenation can be achieved in a manner familiar to the person skilled in the art or as described by way of example in the following examples. Advantageously, the hydroxyl radical is converted firstly into an easily reducible functional group, which is then removed by a reduction reaction to obtain desired compounds of formula X. Thus, for example, the hydroxyl radical of said compounds of formula IX can be converted into the iodine radical in an art-known manner (e.g. by derivatization of the hydroxyl radical with a suitable leaving group, preferably the trifluoromethanesulfonyl group, and subsequent replacement of said leaving group by an iodine nucleophile in a nucleophilic substitution reaction). Thereafter, the iodine radical obtained can be reduced in a manner known to the person skilled in the art using, for example, a suitable hydrogen donor or a suitable hydrogen producing mixture comprising, for example, a suitable metal, preferably zinc, to obtain desired compounds of formula X. Most preferably, said deoxygenation reaction is carried out as described in the following examples employing in the final step sodium iodide and zinc in a one-pot procedure in a suitable solvent, such as dimethoxyethane, at elevated temperature.

Reaction scheme 2:

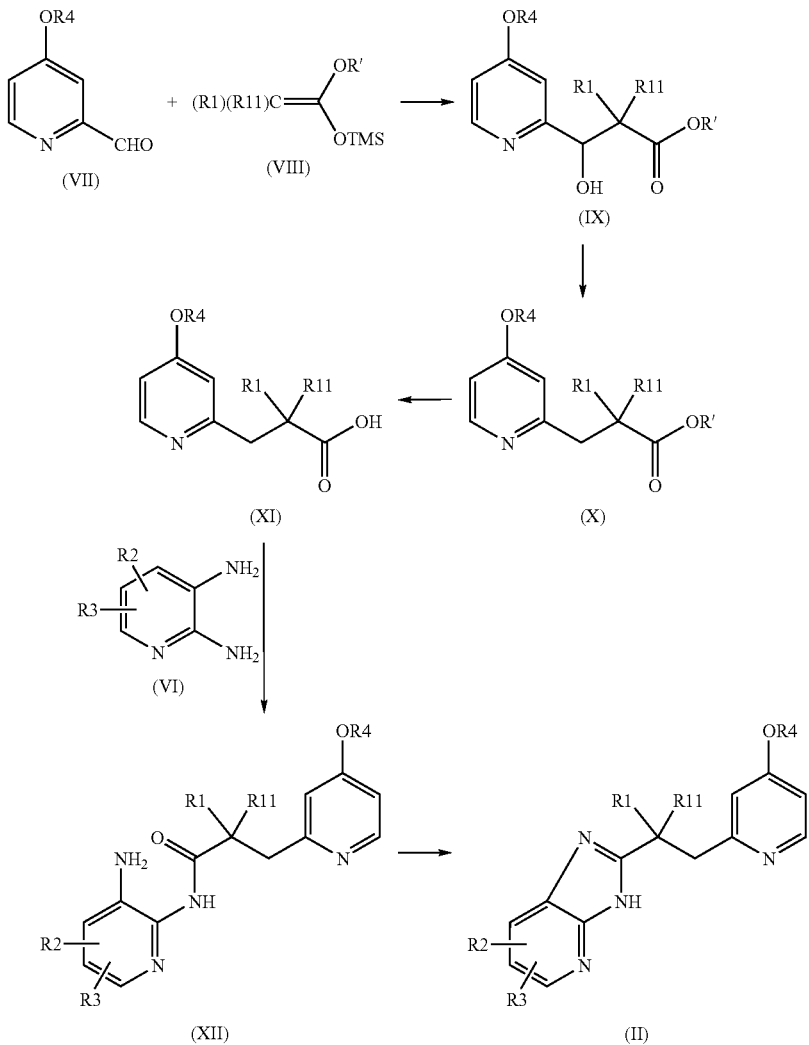

In a third step ester compounds—preferably the methyl ester compounds—of formula X, in which R1 is hydrogen or, preferably, 1-4C-alkyl and R4 and R11 have the meanings indicated above, are saponificated in a manner described in the following examples or as known to the person skilled in the art to give corresponding compounds of formula XI.

In the next step compounds of formula XII, in which R1 is hydrogen or, preferably, 1-4C-alkyl and R2, R3, R4 and R11 have the meanings indicated above, are prepared from compounds of formula XI, in which R1 is hydrogen or, preferably, 1-4C-alkyl and R4 and R11 have the abovementioned meanings, and compounds of formula VI, in which R2 and R3 have the abovementioned meanings, in a manner habitual per se to the person skilled in the art, for example by reaction with amide bond linking reagents known to the person skilled in the art. Exemplary amide bond linking reagents known to the person skilled in the art which may be mentioned are, for example, carbodiimides, azodicarboxylic acid derivatives, uronium salts, N,N'-carbonyldiimidazole or, preferably, phosphonium salts such as, for example, benzotriazol-1-yl-oxy-tris-pyrrolidino-phosphonium hexafluorophosphate.

In the final step compounds of formula XII, in which R1 is hydrogen or, preferably, 1-4C-alkyl and R2, R3, R4 and R11 have the meanings given above, are converted into compounds of formula I, in which R1 is hydrogen or, preferably, 1-4C-alkyl and R2, R3, R4 and R11 have the meanings given above, by cyclocondensation reaction. Said cyclocondensation reaction is carried out in a manner known per se to the person skilled in the art or as described by way of example in the following examples, according to Bischler-Napieralski (e.g. as described in J. Chem. Soc., 1956, 4280-4282) in the presence of a suitable condensing agent, such as, for example, polyphosphoric acid, phosphorus pentachloride, phosphorus pentoxide or phosphorus oxychloride, in a suitable inert solvent, e.g. in a chlorinated hydrocarbon such as chloroform, or in a cyclic hydrocarbon such as toluene or xylene, or another inert solvent such as isopropyl acetate or acetonitrile, or without further solvent using an excess of condensing agent, at reduced temperature, or at room temperature, or at elevated temperature or at the boiling temperature of the solvent or condensing agent used.

Alternatively, compounds of formula XI can be also directly cyclized with compounds of formula VI under suitable conditions (e.g. in polyphosphoric acid at elevated temperature) to give the desired compounds of formula I.

Compounds of formula I, in which R2 is phenyl or R21- and/or R211-substituted phenyl, can be prepared, for example, as described by way of example in the following examples or according to processes known from literature or analogously or similarly thereto, for example starting from the corresponding compounds. of formula I, in which R2 or R3 is preferably iodine or bromine, e.g. according to known metal catalyzed CC-coupling reactions, such as e.g. the Suzuki reaction is. This Suzuki reaction can be carried out as known to the person skilled in the art using, for example, appropriate boronic acids or boronic acid derivatives and suitable metal catalysts, preferably transition metal catalysts (such as, for example, palladium catalysts), optionally, in the presence of an inorganic lithium salt, preferably lithium chloride. Said boronic acids or boronic acid derivatives can be prepared according to art-known manners, e.g. from R21- and/or R211-substituted phenyl haides or triflates using e.g. bis-(pinacolato)-diboron.

Compounds of formula I, in which R2 is 1-4C-alkoxycarbonyl, can be obtained, for example, in a manner known to the person skilled in the art according, for example, a metal catalyzed (e.g. a transition metal catalyzed, preferably palladium catalyzed) carbonylation reaction of the corresponding compounds of formula I, in which R2 or R3 is preferably iodine or bromine, in the presence of a suitable alcohol.

Compounds of formula I, in which R21 is 1-4C-alkylcarbonylamino or phenylsulfonylamino, can be prepared, for example, according to processes known from literature or analogously or similarly thereto starting from the corresponding compounds of formula I, in which R21 is amino, e.g. by acylation or sulfonylation reaction habitual per se to the skilled person.

The compounds according to the invention can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

It is known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. Greene and P. Wuts, "Protective Groups in Organic Synthesis" (John Wiley & Sons, Inc. 1999, $3^{rd}$ Ed.) or in P. Kocienski, "Protecting Groups (Thieme Foundations Organic Chemistry Series N Group" (Thieme Medical Publishers, 2000).

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

Suitably, the conversions mentioned in this invention can be carried out analogously or similarly to methods which are familiar per se to the person skilled in the art, for example, in the manner which is described by way of example in the following examples.

The person skilled in the art knows on the basis of his/her knowledge and on the basis of those synthesis routes, which are shown and described within the description of this invention, how to find other possible synthesis routes for compounds according to this invention. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention.

The following examples illustrate the invention in greater detail, without restricting It. As well, further compounds according to the present invention, of which the preparation is explicitly not described, can be prepared in an analogous way or in a way which is known by a person skilled in the art using customary preparation methods and process techniques.

In the examples, m.p. stands for melting point, h for hours, d for days, min for minutes, TLC for thin layer chromatography, Rf for retention factor, MS for mass spectrum, M for molecular ion, other abbreviations have their meanings customary per se for the skilled person.

The compounds, which are mentioned in the examples as well as their salts are preferred compounds of the invention.

EXAMPLES

Final Products 1. (R,S)-2-[3-(4-Methoxypyridin-2-yl)prop-2-yl]-3H-imidazo[4,5-b]pyridine hydrochloride A solution of 0.59 g of 4-methoxypyridine-2-carbaldehyde (Ashimori et al., Chem. Pharm. Bull. 38, 2446-2458 (1990)) in 19 ml of methanol is treated with 1.9 g of {1-(3H-imidazo[4,5-b]pyridin-2-yl)-ethyl}-triphenyl-phosphonium chloride (compound A1). 3.3 ml of a solution of sodium methanolate in methanol (1.3 M) are added dropwise at 50° C. The reaction mixture is stirred at 50° C. for 4 h and evaporated to dryness. The resulting residue is chomatographed on silica gel using dichloromethane/methanol 20:1 to give 1.75 g of a colorless, amorpheous solid, which is dissolved in 190 ml of methanol. 1.5 ml of glacial acetic acid and 388 mg of palladium on active carbon (10% Pd) are added and the suspension is stirred at room temperature for 2.5 d under hydrogen atmosphere. Then the catalyst is filtered off and the reaction mixture is concentrated to dryness. After chromatographical purification of the residue on silica gel (dichoromethane/methanol 25:1) and evaporation of the eluents, 837 mg of an oil are obtained, which is dissolved in 160 ml of dichloromethane. 2 ml of an ethereal hydrochloric acid solution (2.0 M) are added to the solution under ice-cooling. After lyophillization from dioxane, 0.951 g of the title compound are obtained as a colorless lyophilisate. M.p. 61°-64° C. MS: 269.1 (MH+). TLC: Rf=0.44 (dichloromethane/methanol 10:1).

2. (R.S)-2-[4-(4-Methoxypyridin-2-yl)but-2-yl]-3H-imidazo[4,5-b]pyridine

A solution of 7.2 g of tributyl-{1-(3H-imidazo[4,5-b]pyridin-2-yl)-propyl}-phosphonium chloride (compound A2) in tetrahydrofurane is added to a suspension of 720 mg of sodium hydride (60% strength suspension in paraffin) in 180 ml of tetrahydrofurane. After 15 min stirring, a solution of 0.500 g of 4-methoxypyridine-2-carbaldehyde (Ashimori et al., Chem. Pharm. Bull. 38, 2446-2458 (1990)) in tetrahydrofurane is added dropwise and the reaction mixture is heated at 80° C. for 6 h. The mixture is then evaporated to dryness and the resulting residue chomatographed on silica gel using dichloromethane/methanol 20:1 to give 3.58 g of a colorless, amorpheous solid, which is dissolved as obtained in 200 ml of methanol. 2.9 ml of trifluoracetic acid and 788 mg of palladium on active carbon (10% Pd) are added and the suspension is stirred at room temperature for 2.5 d under hydrogen atmosphere. Then the catalyst is filtered off and the reaction mixture is concentrated to dryness. After chromatographical purification of the residue on silica gel (dichloromethane/methanol 10:1 to 5:1) and evaporation of the eluents, 1.4 g of the title compound are obtained as an oil. MS: 283.1 (MH+). TLC: Rf=0.48 (dichloromethane/methanol 10:1).

3. 2-[2-(4-Methoxypyridin-2-yl)-1,1-dimethyl-ethyl]-3-imidazo[4,5-b]pyridine A solution of 3.56 g of 3-(4-methoxypyridin-2-yl)-2,2-dimethyl-propionic acid (compound A3), 2.05 g of 2,3-diaminopyridine and 12.42 g of benzotriazol-1-yl-oxy-tris-pyrrolidino-phosphonium hexafluorophosphate in 178 ml of pyridine is treated dropwise with 3.5 ml of N,N'-diisopropylethylamine. After complete addition, the reaction mixture is stirred at 40° C. for 22 h. Then the reaction mixture is concentrated to dryness and the residue purified by chromatography on silica gel (dichloromethane/methanol 10:1) to give 4.19 g of the amide intermediate, which is suspended as obtained in 51.5 ml of phosphoroxychloride. The reaction mixture is refluxed for 19 h, evaporated to dryness, the resulting residue is dissolved in 190 ml of water, with the aid of 2 M aqueous sodium hydroxide solution the pH is adjusted to pH 6 and the mixture is extracted four times with each 100 ml of dichloromethane. The organic layers are collected, washed with 100 ml of water and 100 ml of brine, dried using sodium sulfate and concentrated. After chromatographical purification of the residue on silica gel (dichoromethane/methanol 20:1) and evaporation of the eluents, 0.624 of the title compound are obtained as colorless, waxy solid. M.p. 149°-151° C. MS: 283.3 (MH+). TLC: Rf=0.27 (dichloromethane/methanol 10:1).

STARTING MATERIALS

A1. {1-(3H-Imidazo[4,5-b]pyridin-2-yl)-ethyl}-triphenyl-phosphonium chloride 8.66 g of 2-(1-chloroethyl)-3H-imidazo[4,5-b]pyridine (compound B1) are suspended in 40 ml of N,N-dimethylformamide and 120 ml of acetonitrile. 12.6 g of triphenylphosphine are added and the mixture is heated to 150° C. for 17 h. The mixture is concentrated to dryness and the crude product purified by chromatography on silica gel (eluent: dichloromethane/methanol 20:1) to afford 4.16 g of the title compound as an oil. MS: 408.0 (M+).

A2. Tributyl-{1-(3H-imidazo[4.5-b]pyridin-2-yl)-propyl}-phosphonium chloride 8.66 g of 2-(1-chloropropyl)-3H-imidazo[4,5-b]pyridine (compound B2) are suspended in 18 ml of N,N-dimethylformamide and 61 ml of acetonitrile. 6.3 ml of triphenylphosphine are added at 40° C. and the mixture is heated to 90° C. for 16 h. The mixture is concentrated to dryness to give 11.9 g of the title compound as an oil. MS: 362.2 (M+).

A3. 3-(4-Methoxynyridin-2-yl)-2,2-dimethyl-propionic acid

A solution of 1.0 g of 3-(4-methoxypyridin-2-yl)-2,2-dimethyl-propionic acid methyl ester (compound B3) in 52 ml of dioxane is treated dropwise with 12.1 ml of an aqueous solution of lithium hydroxide (290 mg of lithium hydroxide in 12.1 ml of water). After stirring at 50° C. for 3.5 h, the pH is adjusted to pH 6 by addition of aqueous hydrochloric acid (1 M). The solvents are removed in vacuo and the remaining residue is purified by chromatography on silica gel (dichloromethane/methanol 15:1) to obtain 0.864 g of the title compound as colorless, amorpheous solid. M.p. 150°-151° C. MS: 210.2 (MH+). TLC: Rf=0.27 (dichloromethane/methanol 10:1).

B1. 2-(1-Chloroethyl)-3H-imidazo[4,5-b]pyridine 5.2 g of 2,3-diaminopyridine in 209 g of polyphosphoric acid are heated at 120° C. for 0.5 h. The solution is cooled to 80° C. and 4.6 ml of 2-chloropropionitrile are added. Thereafter, the reaction mixture is heated to 180° C. for 2.5 h. After cooling, the polyphosphoric acid is hydrolyzed with water, the mixture is filtered using charcoal and celite and the pH value of the filtrate is adjusted to pH 4 using 9 M aqueous sodium hydroxide solution. The mixture is extracted twice each with 250 ml of ethyl acetate, the combined organic phases are dried using sodium sulfate, concentrated and lyophilized from ethanol/water to give 3.56 g of the title compound as a light brown, amorpheous solid. M.p. 132° C. TLC: Rf=0.60 (dichloromethane/methanol 8:1).

B2. 2-(1-Chloropropyl)-3H-imidazo[4,5-b]pyridine 5.0 g of 2,3-diaminopyridine in 200 g of polyphosphoric acid are heated at 120° C. for 0.5 h. The solution is cooled to 80° C. and 5.7 ml of 2-chlorobutyric acid are added. Thereafter, the reaction mixture is heated to 130° C. for 22 h. After cooling, the polyphosphoric acid is hydrolysed with water, the mixture is filtered using charcoal and celite and the pH value of the filtrate is adjusted to pH 4 using 9 M aqueous sodium hydroxide solution. The mixture is extracted three times each with 200 ml of ethyl acetate, the combined organic phases are dried using sodium sulfate, concentrated and the residue is purified by chromatography on silica gel (eluent: toluene/ethyl acetate 1:1) to give 5.19 g of the title compound as a colorless, amorpheous solid. M.p. 137° C. TLC: Rf=0.50 (dichloromethane/methanol 10:1).

B3.
3-(4-Methoxypyridin-2-yl)-2,2-dimethyl-propionic acid methyl ester 3.0 g of 3-hydroxy-3-(4-methoxypyridin-2-yl)-2,2-dimethyl-propionic acid methyl ester (compound C3), 0.153 g of 4-dimethylaminopyridine and 2.58 ml of N,N'-diisopropyl-ethylamine are dissolved in 80 ml of dichloromethane. Trifluoromethanesulfonic acid anhydride is added dropwise under ice-cooling. The cooling bath is removed and the mixture is stirred at room temperature for 2.5 h. After evaporation in vacuo, the remaining residue is dissolved as obtained in 100 ml of 1,2-dimethoxyethane. 9.37 g of sodium iodide and 16.3 g of activated zinc are added and the mixture is stirred at 100° C. for 1.5 h. The solids are filtered off, the filtrate is diluted with 800 ml of dichloromethane and extracted several times with halfsaturated aqueous sodium chloride solution. The organic layer is dried using sodium sulfate and concentrated. The residue is purified by chromatography on silica gel (toluene/ethyl acetate 2:1) to afford 1.6 g of the title compound as an oil. MS: 224.2 (MH$^+$). TLC: Rf=0.26 (toluene/acetone 2:1).

C3. 3-Hydroxy-3-(4-methoxypyridin-2-yl)-2,2-dimethyl-propionic acid methyl ester A solution of 0.58 g of 4-methoxypyridine-2-carbaldehyde (Ashimori et al., Chem. Pharm. Bull. 38, 2446-2458 (1990)) and 21 mg of scandium trifluoromethanesulfonate in 14 ml of dichloromethane is treated dropwise with 0.9 ml of 1-methoxy-2-methyl-1-trimethylsilyloxypropane under ice-cooling. After 10 min the cooling bath is removed and the mixture is stirred for 18 h. Thereafter, 12 ml of methanol and 12 ml of aqueous hydrochloric acid (3 M) are added and stirring is continued for further 14 h. The solvents are removed in vacuo, the residue is dissolved in dichloromethane and washed with saturated aqueous sodium hydrogencarbonate solution. The organic layer is dried using sodium sulfate and concentrated to give 0.845 g of the title compound as a colorless oil. MS: 240.0 (MH$^+$). TLC: Rf=0.46 (toluene/acetone 2:1).

COMMERCIAL APPLICABILITY

The compounds according to the invention have valuable pharmacological properties which make them commercially utilizable. They are selective inhibitors of the enzyme inducible nitric oxide synthase. Nitric oxide synthases (NO-syntases, NOSs) are enzymes that generate NO and citrulline from the amino acid arginine. In certain pathophysiological situations such as arginine depletion or tetrahydrobiopterin depletion the generation of $O_2^-$ from NO-synthases instead or together with NO has been reported. NO is long known as a signalling molecule in most living organisms including mammals and humans. The most prominent action of NO is it's smooth muscle relaxing activity, which is caused on the molecular level by the activation of soluble guanylate cyclase. In the last years a lot of other enzymes have been shown to be regulated by NO or reaction products of NO.

There exist three isoforms of NO-synthases which fall into two classes and differ in their physiologic functions and molecular properties. The first class, known as constitutive NO-synthases, comprises of the endothelial NO-synthase and the neuronal NO-synthase. Both isoenzymes are expressed constitutively in various cell types, but are most prominent in endothelial cells of blood vessel walls (therefore called endothelial NO-synthase, eNOS or NOS-III) and in neuronal cells (therefore called neuronal NO-synthase, nNOS or NOS-I). Activation of these two enzymes is dependent on $Ca^{2+}$/Calmodulin which is generated by transient increases of the intracellular free $Ca^{2+}$concentration. Activation of constitutive isoforms leads to transient bursts of nitric oxide resulting in nanomolar cellular or tissue NO concentrations. The endothelial isoform is involved in the physiologic regulation of blood pressure. NO generated by the neuronal isoform seems to have neurotransmitter function and the neuronal isoform is among other regulatory processes involved in memory function (long term potentiation).

In contrast to the constitutive isoforms the activation of inducible NO-synthase (iNOS, NOS-II), the sole member of the second class, is performed by transcriptional activation of the iNOS-promoter. Proinflammatory stimuli lead to transcription of the gene for inducible NO-synthase, which is catalytically active without increases in the intracellular $Ca^{2+}$-concentration. Due to the long half live of the inducible NO-synthase and the unregulated activity of the enzyme, high micromolar concentrations of NO are generated over longer time periods. These high NO-concentrations alone or in cooperation with other reactive radicals such as $O_2^-$ are cytotoxic. Therefore, in situations of microbial infections, iNOS is involved in cell killing by macrophages and other immune cells during early nonspecific immune responses.

There are a number of pathophysiological situations which among others are characterized by the high expression of inducible NO-synthase and concomitant high NO or $O_2^-$ concentrations. It has been shown that these high NO concentrations alone or in combination with other radical species lead to tissue and organ damage and are causally involved in these pathophysiologies. As inflammation is characterized by the expression of proinflammatory enzymes, including inducible NO-synthase, acute and chronical inflammatory processes are promising diseases for the therapeutic application of selective inhibitors of inducible NO-synthase. Other pathophysiologies with high NO-production from inducible NO-synthase are several forms of shock (septic, hemorrhagic and cytokine-induced).

It is clear that nonselective NO-synthase inhibitors will lead to cardiovascular and neuronal side effects due to concomitant inhibition of constitutive NO-synthase isoforms.

It has been shown in in-vivo animal models of septic shock that reduction of circulating plasma NO-levels by NO-scavenger or inhibition of inducible NO-synthase restores systemic blood pressure, reduces organ damage and increases survival (deAngelo Exp. Opin. Pharmacother. 19-29, 1999; Redl et al. Shock 8, Suppl. 51, 1997; Strand et al. Crit.Care Med. 26, 1490-1499, 1998). It has also been shown that increased NO production during septic shock contributes to cardiac depression and myocardial dysfunction (Sun et al. J. Mol.Cell Cardiol. 30, 989-997, 1998). Furthermore there are also reports showing reduced infarct size after occlusion of the left anterior coronary artery in the presence of NO-synthase inhibitors (Wang et al. Am. J. Hyperttens. 12, 174-182, 1999). Considerable inducible NO-synthase activity is found in human cardiomyopathy and myocarditis, supporting the hypothesis that NO accounts at least in part for the dilatation and impaired contractility in these pathophysiologies (de Belder et al. Br. Heart. J. 4, 426-430, 1995).

In animal models of acute or chronic inflammation, blockade of inducible NO-synthase by isoform-selective or non-selective inhibitors or genetic knock out improves therapeutic outcome. It is reported that experimental arthritis (Connor et al. Eur. J. Pharmacol. 273, 15-24, 1995) and osteoarthritis (Pelletier et al. Arthritis & Rheum. 41, 1275-1286, 1998), experimental inflammations of the gastrointestinal tract (Zingarelli et al. Gut 45, 199-209, 1999), experimental glomerulonephritis (Narita et al. Lab. Invest. 72, 17-24, 1995), experimental diabetes (Corbett et al. PNAS 90, 8992-8995, 1993), LPS-induced experimental lung injury is reduced by inhibition of inducible NO-synthase or in iNOS-knock out mice (Kristof et al. Am. J. Crit. Care. Med. 158,1883-1889, 1998). A pathophysiological role of inducible NO-synthase derived NO or $O_2^-$ is also discussed in chronic inflammatory diseases such as asthma, bronchitis and COPD.

Furthermore, in models of neurodegenerative diseases of the CNS such as MPTP-induced parkinsonism, amyloid peptide induced Alzheimer's disease (Ishii et al., FASEB J. 14, 1485-1489, 2000), malonate induced Huntington's disease (Connop et al. Neuropharmacol. 35, 459-465, 1996), experimental menengitis (Korytko & Boje Neuropharmacol. 35, 231-237, 1996) and experimental encephalitis (Parkinson et al. J. Mol. Med. 75, 174-186, 1997) a causal participation of NO and inducible NO-synthase has been shown.

Increased iNOS expression has been found in the brains of AIDS victims and it is reasonable to assume a role of iNOS in AIDS related dementia (Bagasra et al. J. Neurovirol. 3 153-167, 1997).

Other studies Implicated nitric oxide as a potential mediator of microglia dependent primary demyelination, a hallmark of multiple sklerosis (Parkinson et al. J. Mol. Med. 75, 174-186,1997).

An inflammatory reaction with concomitant expression of inducible NO-synthase also takes place during cerebral ischemia and reperfusion (ladecola et al. Stroke 27, 1373-1380, 1996). Resulting NO together with $O_2^-$ from infiltrating neutrophils is thought to be responsible for cellular and organ damage. Also, in models of traumatic brain injury (Mesenge et al. J. Neurotrauma 13, 209-214,1996; Wada et al. Neurosurgery 43, 1427-1436, 1998) NO-synthase inhibitors have been show to posses protective properties. A regulatory role for inducible NO-synthase has been reported in various tumor cell lines (Tozer & Everett Clin Oncol. 9. 357-264,1997).

On account of their inducible NO-synthase-inhibiting properties, the compounds according to the invention can be employed in human and veterinary medicine and therapeutics, where an excess of NO or $O_2^-$ due to increases in the activity of inducible NO-synthase is involved. They can be used without limitation for the treatment and prophylaxis of the following diseases:

Acute inflammatory diseases: Septic shock, sepsis, SIRS, hemorrhagic shock, shock states induced by cytokine therapy (IL-2, TNF), organ transplantation and transplant rejection, head trauma, acute lung injury, ARDS, inflammatory skin conditions such as sunburn, inflammatory eye conditions such as uveitis, glaucoma and conjunctivitis.

Chronic inflammatory diseases of peripheral organs and the CNS: gastrointestinal inflammatory diseases such as Crohn's disease, inflammatory bowel disease, ulcerative colitis, lung inflammatory diseases such as asthma and COPD, arthritic disorders such as rheumatoid arthritis, osteoarthritis and gouty arthritis, heart disorders such as cardiomyopathy and myocarditis, artherosklerosis, neurogenic inflammation, skin diseases such as psoriasis, dermatitis and eczema, diabetes, glomerulonephritis; dementias such as dementias of the Alzheimer's type, vascular dementia, dementia due to a general medical condition, such as AIDS-, Parkinson's disease, Huntington's induced dementias, ALS, multiple sklerosis; necrotizing vasculitides such as polyarteritis nodosa, serum sickness, Wegener's granulomatosis, Kawasaki's syndrom; headaches such as migraine, chronic tension headaches, cluster and vascular headaches, post-traumatic stress disorders; pain disorders such as neuropathic pain; myocardial and cerebral ischemia/reperfusion injury.

The compounds may also be useful in the treatment of cancers that express nitric oxide synthase.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions having an iNOS inhibitory activity.

The invention furthermore relates to pharmaceutical compositions for the treatment and/or prophylaxis of the illnesses mentioned, which contain one or more of the compounds according to the invention.

The invention moreover relates to pharmaceutical compositions according to this invention having an iNOS inhibitory activity.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly sufted to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdernal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantagously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for iNOS inhibitors. Topical application forms (such as ointments) for the treatment of dermatoses thus contain the active compounds in a concentration of, for example, 0.1-99%. The dose for administration by inhalation is customarily between 0.1 and 10 mg per day. The customary dose in the case of systemic therapy (p.o.) is between 0.3 and 30 mg/kg per day, (i. v.) is between 0.3 and 30 mg/kg/h.

BIOLOGICAL INVESTIGATIONS

Measurement of Inducible NO-synthase Activity

The assay is performed in 96-well microtiter F-plates (Greiner, Frickenhausen, FRG) in a total volume of 100 μl in the presence of 100 nM calmodulin, 226 μM CaCl$_2$, 477 μM MgCl$_2$, 5 μM flavin-adenine-dinucleotide (FAD), 5 μM flavin mononucleotide (FMN), 0.1 mM NADPH, 7 mM glutathione, 10 μM BH4 and 100 mM HEPES pH 7.2. Arginine concentrations are 0.1 μM for enzyme inhibition experiments. 150000 dpm of [$^3$H]arginine are added to the assay mixture. Enzyme reaction is started by the addition of 4 μg of a crude cytosolic fraction containing human inducible NO-synthase and the reaction mixture is incubated for 45 to 60 min at 37° C. Enzyme reaction is stopped by adding 10 μl of 2M MESbuffer pH 5,0. 50 μp of the incubation mixture are transferred into a MADP N65 filtration microtiter plate (Millipore, Eschborn, FRG) containing already 50 μl of AG-50W-X8 cation exchange resin (Biorad, München, FRG). The resin in the Na loaded form is pre-equilibrated in water and 70 μp (corresponding to 50 μl dry beads) are pipetted under heavy stirring with a 8 channel pipette into the filtration plate. After pipetting 50 μl of the enzyme reaction mixture onto the filtration plates, the plates are placed on a filtration manifold (Porvair, Shepperton, UK) and the flow through is collected in Pico scintillation plates (Packard, Meriden, Conn.). The resin in the filtration plates is washed with 75 μl of water (1×50 μl and 1×25 μl) which is also collected in the same plate as the sample. The total flow through of 125 μl is mixed with 175 μl of Microscint-40 scintillation cocktail (Packard) and the scintillation plate is sealed with TopSeal P-foil (Packard). Scintillation plates are counted in a szintillation counter.

For the measurement of inducible NO-synthaseinhibiting potencies of compounds increasing concentrations of inhibitors were included into the incubation mixture. IC$_{50}$-values were calculated from the percent inhibition at given concentrations by nonlinear least square fitting.

Representative inhibitory values determined for the compounds according to the invention follow from the following table A, in which the compound numbers correspond to the example numbers.

TABLE A

| Inhibition of iNOS activity [measured as $-\log IC_{50}$ (mol/l)] | |
|---|---|
| compound | $-\log IC_{50}$ |
| 1 | 7.15 |

The invention claimed is:
1. Compounds of formula I

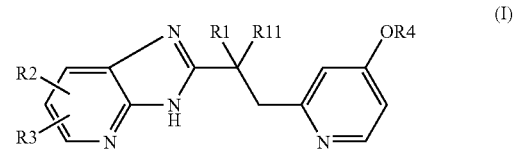

in which
R1 is hydrogen or 1-4C-alkyl,
R2 is hydrogen, halogen, hydroxyl, nitro, amino, 1-7C-alkyl, trifluoromethyl, 3-7C-cycloalkyl, 3-7C-cycloalkyl-1-4C-alkyl, 1-4C-alkoxy, completely or predominantly fluorine-substituted 1-4C-alkoxy, 1-4C-alkoxy-1-4C-alkyl, 1-4C-alkoxy-1-4C-alkoxy, 1-4C-alkoxycarbonyl, mono- or di-1-4C-alkylaminocarbonyl, mono- or di-1-4C-alkylaminosulfonyl, 1-4C-alkylcarbonylamino, 1-4C-alkylsulfonylamino, phenyl, R21- and/or R211-substituted phenyl, phenyl-1-4C-alkyl, phenyl-1-4C-alkyl wherein the phenyl moiety is substituted by R22, phenyl-1-4C-alkoxy, pyridyl, pyridyl substituted by R23, pyridyl-1-4C-alkyl, pyridyl-1-4C-alkyl wherein the pyridyl moiety is substituted by R24, in which R21 is cyano, halogen, carboxyl, 1-4C-alkyl, 1-4C-alkoxy, aminocarbonyl, mono- or di-1-4C-alkyaminocarbonyl, 1-4C-alkylcarbonylamino, 1-4C-alkoxycarbonyl, aminosulfonyl, mono- or di-1-4C-alkylaminosulfonyl, amino, mono- or di-1-4C-alkylamino, trifluoromethyl, hydroxyl, phenylsulfonylamino or phenyl-1-4C-alkoxy, R211 is halogen or 1-4C-alkoxy, R22 is halogen, 1-4C-alkyl or 1-4C-alkoxy, R23 is halogen, 1-4C-alkyl or 1-4C-alkoxy, R24 is halogen, 1-4C-alkyl or 1-4C-alkoxy, R3 is hydrogen, halogen, 1-4C-alkyl or 1-4C-alkoxy, R4 is 1-4C-alkyl, R11 is 1-4C-alkyl, and the salts, the N-oxides and the salts of the N-oxides of these compounds.

2. Compounds according to claim 1 in which

R1 is hydrogen or 1-4C-alkyl,

R2 is hydrogen,

R3 is hydrogen,

R4 is methyl,

R11 is 1-4C-alkyl, and the salts, the N-oxides and the salts of the Noxides of these compounds.

3. Compounds according to claim 1 in which either $R_1$ is hydrogen,

R2 is hydrogen,

R3 is hydrogen,

R4 is methyl, and

R11 is methyl or ethyl, or $R_1$ is methyl,

R2 is hydrogen,

R3 is hydrogen,

R4 is methyl, and

R11 is methyl, and the salts, the N-oxides and the salts of the N-oxides of these compounds.

4. Compounds of formula I according to claim 1 in which R4 is methyl, and the salts, the N-oxides and the salts of the N-oxides of these compounds.

5. Compounds of formula I according to claim 1 in which R1 is hydrogen, R4 is methyl and R11 is methyl, and the salts, the N-oxides and the salts of the N-oxides of these compounds.

6. Pharmaceutical compositions containing one or more compounds of formula I according to claim 1 together with the usual pharmaceutical auxiliaries and/or excipients.

* * * * *

UNITED STATES PATENT AND TRADEMARK OFFICE
CERTIFICATE OF CORRECTION

PATENT NO. : 7,329,677 B2
APPLICATION NO. : 10/573203
DATED : February 12, 2008
INVENTOR(S) : Fuchss It is certified that error appears in the above-identified patent and that said Letters Patent is hereby corrected as shown below:

Claim 1, Column 20, Line 43,
Please delete "Compounds of"
and
replace with
-- A compound of --

Claim 1, Column 21, Line 1,
Please delete "pyridyl-1-4C-alkyl, pyridyl-1-4C-alkyl"
and
replace with
-- pyridyl-l-4C-alkyl, or pyridyl-1-4C-alkyl --

Claim 1, Column 21, Line 4,
Please delete "ami nocarbonyl,"
and
replace with
-- aminocarbonyl, --

Claim 1, Column 21, Lines 17-18,
Please delete "and the salts, the N-oxides and the salts of the N-oxides of these compounds"
and
replace with
-- or a salt, N-oxide or a salt of an N-oxide thereof --

Claim 2, Column 21, Line 19,
Please delete "Compounds"
and
replace with
-- The compound --

Claim 2, Column 21, Lines 25-26,
Please delete "and the salts, the N-oxides and the salts of the Noxides of these compounds"
and
replace with
-- or a salt, N-oxide or a salt of an N-oxide thereof --

UNITED STATES PATENT AND TRADEMARK OFFICE
CERTIFICATE OF CORRECTION

PATENT NO. : 7,329,677 B2
APPLICATION NO. : 10/573203
DATED : February 12, 2008
INVENTOR(S) : Fuchss It is certified that error appears in the above-identified patent and that said Letters Patent is hereby corrected as shown below:

Claim 3, Column 22, Line 1,
Please delete "Compounds"
and
replace with
-- The compound --

Claim 3, Column 22, Line 3,
Please delete "$R_1$"
and
replace with
-- R1 --

Claim 3, Column 22, Line 9,
Please delete "$R_1$"
and
replace with
-- R1 --

Claim 3, Column 22, Lines 14-15,
Please delete "and the salts, the N-oxides and the salts of the N-oxides of these compounds"
and
replace with
-- or a salt, N-oxide or a salt of an N-oxide thereof --

Claim 4, Column 22, Line 16,
Please delete "Compounds"
and
replace with
-- The compound --

Claim 4, Column 22, Lines 17-18,
Please delete "and the salts, the N-oxides and the salts of the N-oxides of these compounds"
and
replace with
-- or a salt, N-oxide or a salt of an N-oxide thereof --

UNITED STATES PATENT AND TRADEMARK OFFICE
CERTIFICATE OF CORRECTION

PATENT NO. : 7,329,677 B2
APPLICATION NO. : 10/573203
DATED : February 12, 2008
INVENTOR(S) : Fuchss It is certified that error appears in the above-identified patent and that said Letters Patent is hereby corrected as shown below:

Claim 5, Column 22, Line 19,
Please delete "Compounds"
and
replace with
-- The compound --

Claim 5, Column 22, Lines 20-22,
Please delete "and the salts, the N-oxides and the salts of the N-oxides of these compounds"
and
replace with
-- or a salt, N-oxide or a salt of an N-oxide thereof --

Claim 6, Column 22, Line 23,
Please delete "Pharmaceutical compositions"
and
replace with
-- A pharmaceutical composition --

Claim 6, Column 22, Lines 24-25,
Please delete "claim 1 together with the usual pharamceutical auxiliaries and/or excipients"
and
replace with
-- claim 1, or a pharmaceutically acceptable salt, N-oxide or a salt of an N-oxide thereof, together with a pharmaceutically suitable auxiliary and/or excipient --

Signed and Sealed this

Second Day of September, 2008

JON W. DUDAS
*Director of the United States Patent and Trademark Office*